(12) United States Patent
Viswanathan et al.

(10) Patent No.: US 8,231,618 B2
(45) Date of Patent: Jul. 31, 2012

(54) MAGNETICALLY GUIDED ENERGY DELIVERY APPARATUS

(75) Inventors: Raju R. Viswanathan, St. Louis, MO (US); Gareth T. Munger, St. Louis, MO (US); Ashwini K. Pandey, Marlborough, MA (US); Christopher D. Minar, New Prague, MN (US)

(73) Assignee: Stereotaxis, Inc., St. Louis, MO (US)

( * ) Notice: Subject to any disclaimer, the term of this patent is extended or adjusted under 35 U.S.C. 154(b) by 692 days.

(21) Appl. No.: 12/265,013

(22) Filed: Nov. 5, 2008

(65) Prior Publication Data

US 2009/0138009 A1    May 28, 2009

Related U.S. Application Data

(60) Provisional application No. 60/985,640, filed on Nov. 5, 2007.

(51) Int. Cl.
*A61B 18/14* (2006.01)
(52) U.S. Cl. .......................................... 606/41
(58) Field of Classification Search ...................... 606/41
See application file for complete search history.

(56) References Cited

U.S. PATENT DOCUMENTS

| | | | | |
|---|---|---|---|---|
| 4,790,311 | A | * | 12/1988 | Ruiz ................................. 606/28 |
| 5,425,731 | A | * | 6/1995 | Daniel et al. ..................... 606/28 |
| 5,555,618 | A | * | 9/1996 | Winkler ........................... 29/825 |
| 5,654,864 | A | | 8/1997 | Ritter et al. |
| 5,766,167 | A | * | 6/1998 | Eggers et al. .................... 606/46 |
| 5,931,818 | A | | 8/1999 | Werp et al. |
| 5,935,124 | A | * | 8/1999 | Klumb et al. ..................... 606/42 |
| 6,009,877 | A | * | 1/2000 | Edwards ........................ 128/898 |
| 6,014,580 | A | | 1/2000 | Blume et al. |
| 6,015,414 | A | | 1/2000 | Werp et al. |
| 6,128,174 | A | | 10/2000 | Ritter et al. |
| 6,148,823 | A | | 11/2000 | Hastings |
| 6,152,933 | A | | 11/2000 | Werp et al. |
| 6,157,853 | A | | 12/2000 | Blume et al. |
| 6,212,419 | B1 | | 4/2001 | Blume et al. |

(Continued)

OTHER PUBLICATIONS

International Search Report and Written Opinion for Corresponding PCT/US08/82537 Date of Mailing: Jan. 9, 2009 pp. 10.

(Continued)

*Primary Examiner* — Michael Peffley
*Assistant Examiner* — Daniel Fowler
(74) *Attorney, Agent, or Firm* — Harness, Dickey & Pierce, P.L.C.

(57) ABSTRACT

This invention describes an energy delivery apparatus for delivering electrical energy at a target location, said energy delivery apparatus being usable in combination with a magnetic field and comprising an electrical conductor having a substantially elongated configuration; an electrode for delivering electrical energy at the target location, with the electrode being electrically coupled to the electrical conductor and having an exposed surface with at least a portion of the exposed surface having one of its principal radii of curvature smaller than 0.35 mm; an insulating dielectric coating along a substantial portion of the length of the electrical conductor, with the dielectric coating having a dielectric constant smaller than about 3; at least one guiding element mounted to the electrical conductor, with at least one of the guiding elements including a magnetically responsive material. The magnetic field is used to move the guiding element in order to position the electrode substantially adjacent to the target location.

12 Claims, 3 Drawing Sheets

U.S. PATENT DOCUMENTS

| | | |
|---|---|---|
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,569,162 B2 * | 5/2003 | He ................................ 606/41 |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 7,276,044 B2 | 10/2007 | Ferry et al. |
| 7,286,034 B2 | 10/2007 | Creighton |
| 7,305,263 B2 | 12/2007 | Creighton, IV |
| 7,313,429 B2 | 12/2007 | Creighton, IV et al. |
| 7,341,063 B2 | 3/2008 | Garbibaldi et al. |
| 7,346,379 B2 | 3/2008 | Eng et al. |
| 7,389,778 B2 | 6/2008 | Sabo et al. |
| 7,416,335 B2 | 8/2008 | Munger |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2003/0125752 A1 | 7/2003 | Werp et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0176804 A1 * | 9/2004 | Palti ................................ 607/2 |
| 2004/0186376 A1 | 9/2004 | Hogg et al. |
| 2004/0215184 A1 * | 10/2004 | Eggers et al. .................... 606/41 |
| 2004/0249262 A1 | 12/2004 | Werp et al. |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0065435 A1 | 3/2005 | Rauch et al. |
| 2005/0096589 A1 | 5/2005 | Shachar |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0123964 A1 | 5/2007 | Davies et al. |
| 2007/0135804 A1 | 6/2007 | Ritter et al. |
| 2007/0137656 A1 | 6/2007 | Viswanathan |
| 2007/0146106 A1 | 6/2007 | Creighton, IV |
| 2007/0149946 A1 | 6/2007 | Viswanathan et al. |
| 2007/0161882 A1 | 7/2007 | Pappone |
| 2007/0167720 A1 | 7/2007 | Viswanathan et al. |
| 2007/0179492 A1 | 8/2007 | Pappone |
| 2007/0197899 A1 | 8/2007 | Ritter et al. |
| 2007/0197901 A1 | 8/2007 | Viswanathan |
| 2007/0197906 A1 | 8/2007 | Ritter |
| 2007/0225589 A1 | 9/2007 | Viswanathan |
| 2007/0250041 A1 | 10/2007 | Werp |
| 2007/0270686 A1 | 11/2007 | Ritter et al. |
| 2008/0004595 A1 | 1/2008 | Viswanathan et al. |
| 2008/0006280 A1 | 1/2008 | Alberto et al. |
| 2008/0015427 A1 | 1/2008 | Kastelein et al. |

| | | |
|---|---|---|
| 2008/0015670 A1 | 1/2008 | Pappone |
| 2008/0016677 A1 | 1/2008 | Creighton, IV |
| 2008/0016678 A1 | 1/2008 | Creighton, IV et al. |
| 2008/0039705 A1 | 2/2008 | Viswanathan |
| 2008/0039830 A1 | 2/2008 | Munger et al. |
| 2008/0043902 A1 | 2/2008 | Viswanathan |
| 2008/0045892 A1 | 2/2008 | Ferry et al. |
| 2008/0047568 A1 | 2/2008 | Ritter et al. |
| 2008/0055239 A1 | 3/2008 | Garibaldi et al. |
| 2008/0058608 A1 | 3/2008 | Garibaldi et al. |
| 2008/0058609 A1 | 3/2008 | Garibaldi et al. |
| 2008/0058963 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0064969 A1 | 3/2008 | Kastelein |
| 2008/0065061 A1 | 3/2008 | Viswanathan |
| 2008/0077007 A1 | 3/2008 | Hastings et al. |
| 2008/0092993 A1 | 4/2008 | Creighton, IV |
| 2008/0097200 A1 | 4/2008 | Blume et al. |
| 2008/0114335 A1 | 5/2008 | Flickinger et al. |
| 2008/0132910 A1 | 6/2008 | Pappone |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2008/0319303 A1 | 12/2008 | Sabo et al. |
| 2009/0012821 A1 | 1/2009 | Besson et al. |

OTHER PUBLICATIONS

Magnetic Manipulation Instrumentation for Medical Physics Research Authors: G. T. Gillies, r. C. Ritter, W. C. Broaddus, M. S. Grady, M. A. Howard, III, R. G. McNeil 1994 American Institute of Physics Rev. Sci. Instrum. vol. 65, No. 3, Mar. 1994 pp. 533-562.

* cited by examiner

MAGNETICALLY GUIDED ENERGY DELIVERY APPARATUS

CROSS-REFERENCE TO RELATED APPLICATIONS

This application claims priority to U.S. Provisional Patent Application Ser. No. 60/985,640 filed Nov. 5, 2007. The disclosure of the above-referenced application is incorporated herein by reference.

FIELD OF THE INVENTION

The present invention relates generally to methods and devices to deliver energy in interventional and surgical applications. In particular, the present invention is concerned with a magnetically guidable energy delivery apparatus and methods of using same.

BACKGROUND OF THE ART

Many medical interventions rely on the delivery to a target location of energy, such as electrical energy, inside the body of a patient. For example, an occlusion in a blood vessel may be vaporized, at least partially, or generally dissociated, by delivering a suitable electrical current to the occlusion.

There currently exist magnetically guided guide wires, which are typically long and relatively thin wires at the end of which a magnet is located. The guide wire is typically used in conjunction with a catheter that is slid over the guide wire after the wire has been advanced through a desired path. In use, the guide wire is protruding over a relatively small distance in front of the catheter when there is a need to either steer the catheter at a junction, or guide the catheter through a relatively tortuous path. Then, a magnetic field may be applied to guide the guide wire through a predetermined path and thereafter slide the catheter over the guide wire. However, such guide wires are typically not well suited to the targeted application of electrical energy as, for example, they are not electrically insulated.

SUMMARY OF THE INVENTION

There is a need to provide novel remotely steerable devices that can not only be navigated efficiently, but can also mechanically support and guide other therapeutic devices, as well as deliver energy effectively to a desired lesion site in the patient anatomy. The present invention provides such a method and an apparatus.

In a broad aspect, the invention provides an energy delivery apparatus for delivering electrical energy at a target location, the energy delivery apparatus being usable in combination with a magnetic field. The energy delivery apparatus includes a guide wire that acts as an electrical conductor, in addition to having sufficient flexibility in its distal portion to be navigated efficiently through tortuous anatomy, as well as sufficient mechanical stiffness proximally thereafter to be able to support a range of therapeutic devices. An electrode at the wire tip is used for delivering the electrical energy at the target location, the electrode being electrically coupled to the electrical conductor and located at a predetermined location therealong; also included is a guiding element mounted to the electrical conductor in a spaced apart relationship relative to the electrode, the guiding element including a magnetically responsive material. The energy delivery apparatus is constructed such that a movement of the guiding element causes a corresponding movement of the electrode. An external magnetic field is applied to move the guiding element in order to position the electrode substantially adjacent to the target location.

Spacing apart the guiding element from the electrode may be advantageous in some circumstances because it can prevent de-magnetization of the magnetically responsive material present in the guiding element in case there is significant heating of materials substantially adjacent the electrode when electrical current is delivered by the electrode.

In some embodiments of the invention, a heat shield is located between the electrode and the guiding element. This improves the thermal insulation between these two components and therefore, further prevents de-magnetization of the magnetically responsive material present in the guiding element.

In another broad aspect, the invention provides a method for delivering electrical energy at a target location using an energy delivery apparatus, the method using a magnetic field, the target location being located in a body of a patient, the body including a body vessel, the energy delivery apparatus being substantially elongated, the energy delivery apparatus defining an apparatus proximal end and a substantially longitudinally opposed apparatus distal end, the energy deliver apparatus including a substantially elongated electrical conductor, an electrode electrically coupled to the electrical conductor and a magnetically responsive material mounted to the electrical conductor. The method includes: inserting the apparatus distal end into the body vessel; applying the magnetic field to exert a magnetic force onto the magnetically responsive material so as to move the electrode; guiding the electrode to an electrode location, the electrode location being substantially adjacent to the target location; and delivering the electrical energy at the target location through the electrode.

In yet another broad aspect, the invention provides an energy delivery apparatus for delivering electrical energy at a target location, the energy delivery apparatus being usable in combination with a magnetic field. The energy delivery apparatus includes an electrical conductor, the electrical conductor having a substantially elongated configuration; an electrode for delivering the electrical energy at the target location, the electrode being electrically coupled to the electrical conductor; and a guiding element mounted to the electrical conductor, the guiding element including a magnetically responsive material. The energy delivery apparatus is constructed such that a movement of the guiding element causes a corresponding movement of the electrode. An externally applied magnetic field is used to move the guiding element in order to position the electrode substantially adjacent to the target location.

Other objects, advantages and features of the present invention will become more apparent upon reading of the following non-restrictive description of certain embodiments thereof, given by way of example only with reference to the accompanying drawings.

DETAILED DESCRIPTION

Figure 1:
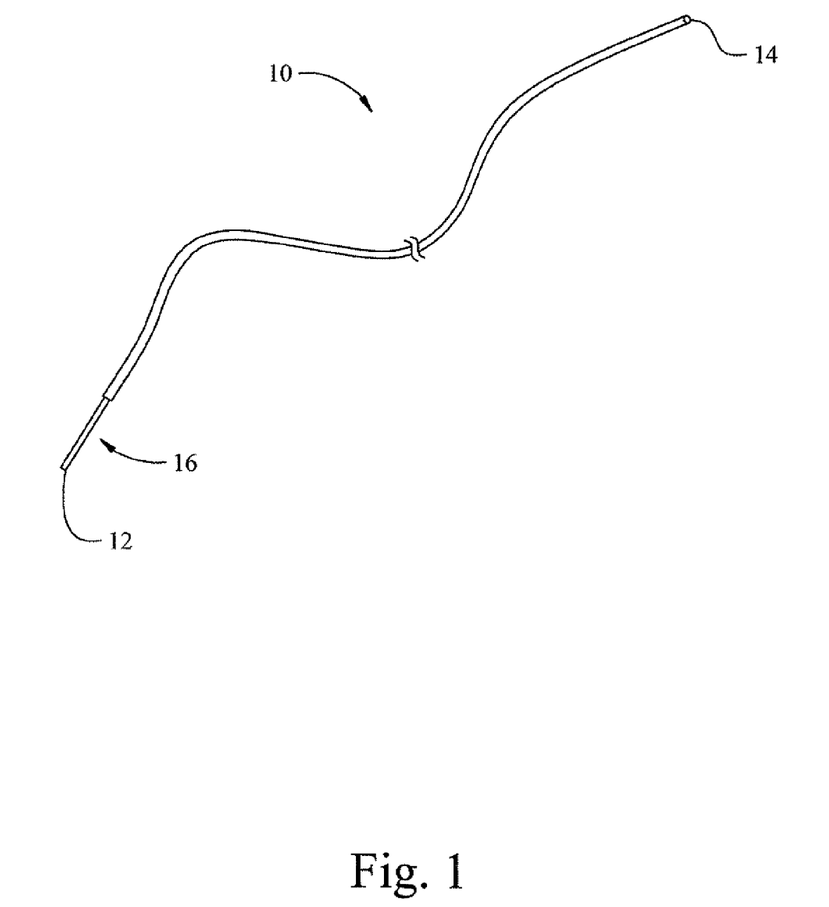
FIG. 1, is a side elevation view, illustrates an energy delivery apparatus in accordance with an embodiment of the present invention.

With reference to FIG. 1, there is shown an embodiment of an energy delivery apparatus in the form of a guide wire device 10 for delivering electrical energy at a target location. For example, and non-limitingly, the target location is located inside the body of a patient. The energy delivery apparatus 10 is usable in combination with a magnetic field (not shown in the drawings). The magnetic field allows to guide the energy delivery apparatus 10 so that a predetermined component or portion of the energy delivery apparatus, such as for example an electrode, is located substantially adjacent the target location. The energy delivery apparatus 10 is substantially elongated and defines an apparatus proximal end 12 and a substantially longitudinally opposed apparatus distal end 14. The apparatus proximal end 12 is typically configured and sized so as to be couplable to a conventional source of electrical energy. Furthermore the distal portion of the guide wire apparatus includes at least one piece of magnetic material that can react to an applied external magnetic field. Thus when a relatively homogeneous magnetic field is applied to the device, the at least one tip magnet reacts so as to attempt to align with the applied magnetic field as closely as it can, subject to any elastic restoring forces.

Figure 2:
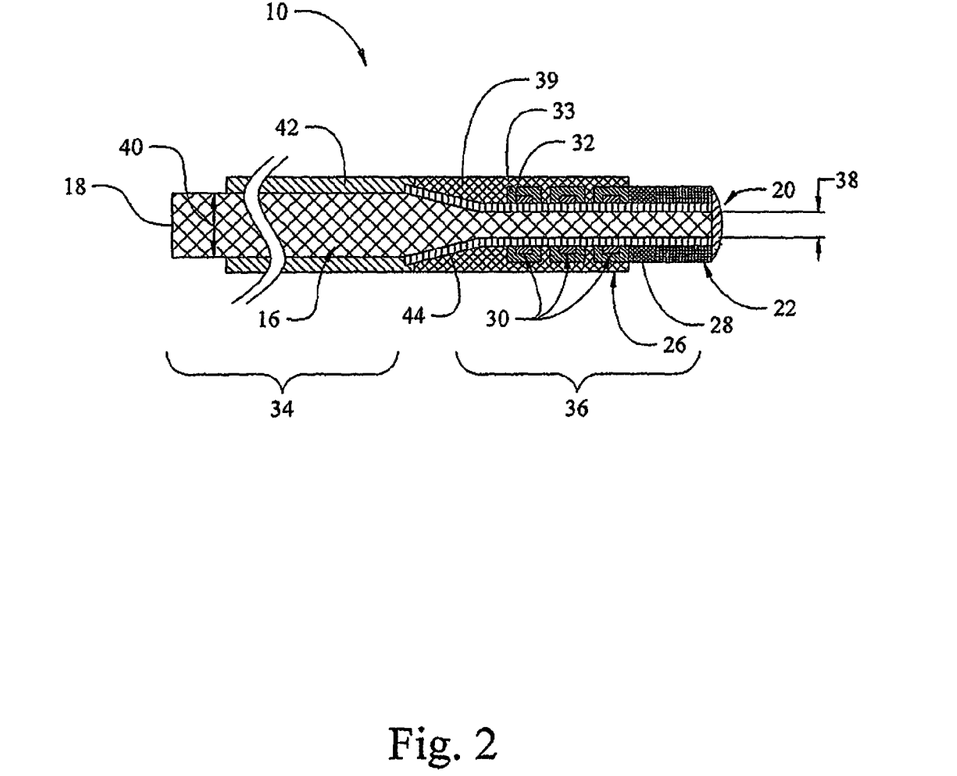
FIG. 2, is a partial side cross-sectional view, illustrates the energy delivery apparatus shown in FIG. 1.

Referring to FIG. 2, the energy delivery apparatus 10 includes a substantially elongated electrical conductor 16, which may be any suitable conductor, such as a wire or a cable made out of a suitable electrically conducting material, such as for example, Nitinol, stainless steel, gold, platinum, titanium, silver or alloys thereof. The electrical conductor 16 is substantially elongated and defines a conductor proximal end 18 and a substantially longitudinally opposed conductor distal end 20. An electrode 22 is electrically coupled to the electrical conductor 16 and located at a predetermined location therealong, for example adjacent to conductor distal end 20. The electrode 22 is provided for delivering electrical energy at a target location.

A guiding element 26 is mechanically coupled or otherwise directly or indirectly mounted to the electrical conductor 16 in a substantially spaced apart relationship relative to the electrode 22. The guiding element 26 includes a magnetically responsive material. The energy delivery apparatus 10 is constructed such that movements of the guiding element 26 cause corresponding movements of the electrode 22. The magnetic field is therefore usable to move the guiding element 26 in order to position the 22 substantially adjacent to the target location. A more detailed description of a method of magnetic navigation is disclosed in U.S. Pat. No. 6,755,816 B2 (issued on 29 Jun. 2004), which is hereby incorporated by reference in its entirety.

Spacing apart the guiding element 26 from the 22 ensures that any temperature increase caused by the delivery of electrical energy to the target location only minimally influences the magnetic properties of the guiding element 26. Indeed, some materials, such as for example permanently magnetized materials, have a temperature over which they lose their magnetic properties. For many of the magnetically responsive materials that are suitable for use with the energy delivery apparatus 10, this temperature is sufficiently low that thermal effects caused by the delivery of the electrical energy could contribute significantly to this loss of magnetic properties.

In the embodiment of the invention shown in FIG. 2, the guiding element 26 is substantially longitudinally spaced apart from the electrode 22. More specifically, the electrode 22 is located distally relatively to the guiding element 26. For example, the electrode 22 is located substantially adjacent to the conductor distal end 20. It should be noted that while the electrode 22 shown in FIG. 2 is substantially cylindrical and extends substantially radially outwardly from the electrical conductor 16, it is also within the scope of the invention to have an electrode that is formed integrally by a section of the outermost surface of the electrical conductor 16.

Figure 3A:
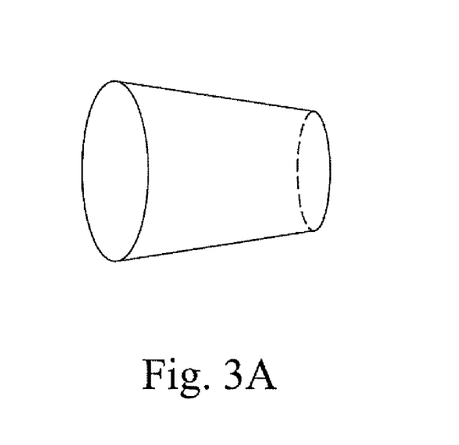
FIG. 3A, is a schematic view of a symmetrically tapered electrode tip.
Figure 3B:
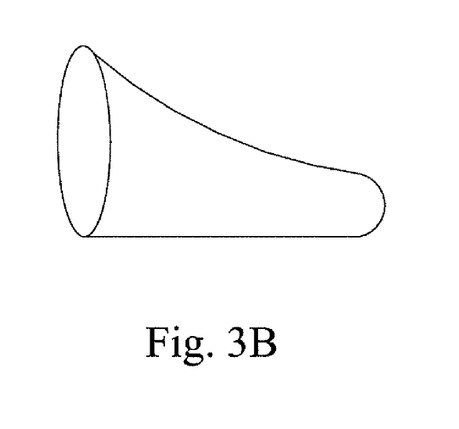
FIG. 3B, is a schematic view of an asymmetrically tapered electrode tip.

The electrode at the tip of the guide wire can be shaped in some embodiments to decrease the surface area and/or to provide a region of relatively high curvature. Such geometrical shaping helps to generate relatively large electric fields in close proximity to the electrode when a voltage is applied to the electrode by connecting the proximal end to a source of electrical energy. In one embodiment, the electrode can be cylindrical in shape with a diameter of about 0.3 mm, corresponding to a curvature of 3.33 $mm^{-1}$. Alternatively, the exposed surface area of the electrode, regardless of shape, can be preferably smaller than 1 $mm^2$ and more preferably smaller than 0.5 $mm^2$ and still more preferably smaller than 0.25 $mm^2$. In another embodiment the tip electrode can be symmetrically tapered as shown in FIG. 3A, such that the distal end of the electrode has a radius that is at least 10% smaller than the radius of the proximal end of the electrode. In yet another embodiment the electrode can be tapered asymmetrically as shown in FIG. 3B, resulting in a tip curvature at the most distal end of at least 4 $mm^{-1}$. In one embodiment, at least a portion of the proximal section of the electrode can be covered by insulating dielectric material.

The energy delivery apparatus 10 includes an electrically insulating material substantially covering the electrical conductor 16 and made of a dielectric material with a relative dielectric constant preferably smaller than about 3. Non-limiting examples of potential insulation materials include Teflons®, such as polytetrafluoroethylene (PTFE), fluorinated ethylene propylene copolymer (FEP), perfluoroalkoxy (PFA), or ethylene and tetrafluoroethylene copolymer (ETFE, for example Tefzel®), or coatings other than Teflons®, such as polyetheretherketone plastics (PEEK™), parylene, certain ceramics, or polyethylene terpthalate (PET), or a range of other polymers. It should be emphasized that these materials are listed as non-limiting examples only, and any other suitable material with the appropriate dielectric properties could also be used as insulation. In some embodiments, the electrically insulating material forms a layer that extends substantially radially outwardly from the electrical conductor 16. The electrically insulating material is described in further details in the following.

In some embodiments of the invention, the energy delivery apparatus 10 further includes a heat shield 28 made out of a substantially thermally insulating material, for example, and non-limitingly, polytetrafluoroethylene (PTFE), which has a thermal conductivity of about 0.3 W/m-K. In this embodiment, the heat shield 28 may have a thickness of at least about 0.025 mm. In other embodiments, the thickness of the heat shield 28 may vary, depending on the thermal conductivity of the material being used. The heat shield 28 is located, at least in part, between the electrode 22 and the guiding element 26. The heat shield 28 is provided for further thermally insulating the guiding element 26 from the electrode 22 and from heat produced by the delivery of electrical energy through the electrode 22.

In some embodiments of the invention, the heat shield includes polytetrafluoroethylene (PTFE). The use of PTFE is advantageous as, in addition to having suitable thermal insulation properties, PTFE is also an electrically insulating material (having a dielectric strength of about 24 kV/mm) and, therefore, contributes to the prevention of arcing between the electrode 22 and any metallic material that may be present in the guiding element 26. In alternate embodiments, other materials, such as for example, Zirconium Oxide, may be used for heat shield 28.

In the embodiment of the invention shown in FIG. 2, the heat shield 26 extends substantially longitudinally from both the guiding element 26 and the electrode 22. In other words, the heat shield 28 substantially fills a gap between the electrode 22 and the guiding element 26. However, in alternative embodiments of the invention, the heat shield 28 extends substantially longitudinally only from one of the guiding element 26 and the electrode 22 or, alternatively, the heat shield 26 does not contact either one of the guiding element 26 and the electrode 22. An advantage of having a heat shield 28 that extends from and contacts both the electrode 22 and the guiding element 26 is that the electrodes 22 are then located as close as possible to the guiding element 26 which therefore helps in improving the precision with which the electrode 22 is guided through the magnetic field interacting with the guiding element 26.

In some embodiments of the invention, the guiding element 26 includes one or more guiding components 30. For example, as shown in FIG. 2, the guiding element 26 includes three substantially longitudinally spaced apart guiding components 30. Each of the guiding components 30 includes a respective magnetically responsive material. In the illustrated embodiment, having the guiding components 30 spaced apart provides additional flexibility around guiding element 26. In some embodiments of the invention, the guiding components 30 are substantially adjacent to each other. In such a configuration, having more than one guiding component allows to have a guiding element that is more responsive to a given magnetic field while ensuring that the radial extension of the guiding element 26 is relatively small. In alternative embodiments of the invention, the guiding components 30 are spaced apart further from each other in a manner allowing to control the shape of the electrical conductor 16. In other words, in these embodiments, it is possible to apply magnetic fields having different orientations substantially adjacent each of the guiding components 30 to control the shape of the electrical conductor 16. While the use of three guiding components 30 in the energy delivery apparatus 10 has been found to be optimal using commonly available magnetic materials, it is within the scope of the invention to have guiding elements 22 having less than three or more than three guiding components 30.

In some embodiments of the invention, the guiding components 30 include permanently magnetized components such as, for example a neodymium magnet, a platinum-cobalt magnet, or any other suitable heat-resistant magnets. A heat resistant magnet, for the purpose of this description, is defined as a magnet that has relatively low probabilities of being adversely affected in its magnetization by a delivery of electrical energy through the electrode 22. However, in alternative embodiments of the invention, each of the guiding components 30 includes any other suitable magnetically responsive material such as, for example, a ferromagnetic, a paramagnetic, or a diamagnetic material.

Also, in some embodiments of the invention, each of the guiding components 30 includes a substantially annular magnet 32 coated by a protective coating 33, such as a parylene coating. The protective coating 33 ensures biocompatibility between the guiding components 30 and the body in which the energy delivery apparatus 10 is inserted. In alternative embodiments of the invention, the protective coating 33 is any other suitable biocompatible coating. Also, in some embodiments of the invention, an additional coating 39 is provided over one or more of the electrode 22, the heat shield 28 and the guiding components 30. This additional coating 39 may help to secure components 30 in place, it may provide electrical insulation, it may provide additional lubricity (e.g. it may be hydrophilic) and may be filled with a radiopaque filler for improved visualization. In one particular embodiment, the additional coating 39 is made of a polyurethane, for example Tecoflex®, Carbothane® or carboflex and it extends between the individual components 30 such that the guiding element 26 has a substantially longitudinally constant outer diameter.

In some embodiments of the invention, the electrical conductor 16 defines a conductor wider section 34 and a conductor narrower section 36. The conductor narrower section 36 is positioned distally relatively to the conductor wider section 34. The conductor wider section 34 has a cross-sectional area that is substantially larger than the cross-sectional area of the conductor narrower section 36. The conductor narrower section 36 increases the flexibility of the distal end section of the energy delivery apparatus 10 while the conductor wider section 34 allows for maintaining a relatively large rigidity at the proximal end of the energy delivery apparatus 10. This allows to relatively easily steer the conductor distal end 20 while allowing to relatively easily manipulate the energy delivery apparatus into the body vasculature of the patient. In addition, having a conductor wider section 34 of a relatively large cross-sectional area reduces ohmic losses when the electrical current is delivered to the electrode 22.

In some embodiments of the invention, the conductor wider and narrower sections 34 and 36 are substantially cylindrical and define respective conductor wider and narrower section outer diameters 38 and 40. Therefore, in these embodiments, the conductor wider section outer diameter is substantially larger than the conductor narrower section outer diameter. When the conductor material is Nitinol, a conductor narrower section having a conductor narrower section outer diameter of about 0.0027 inches or less has been found to be particularly well suited for use in relatively small body vessels.

In alternative embodiments of the invention, the electrical conductor 16 is made more flexible substantially adjacent the conductor distal end 20 than substantially adjacent the conductor proximal end 18 in any other suitable manner such as, for example, by using different materials for manufacturing the conductor proximal and distal regions. It has been found that one suitable material for manufacturing the actual conductor 16 is Nitinol. Indeed, Nitinol shows super-elastic properties and is therefore particularly suitable for applying relatively large deformations thereto in order to guide the energy delivery apparatus 10 through relatively tortuous paths. Also, since the energy delivery apparatus 10 typically creates channels inside biological tissues through radio frequency perforations, in some embodiments of the invention, the energy delivery apparatus 10 typically does not need to be very rigid. In other embodiments, it is desirable that at least a substantial proximal section of the energy delivery apparatus have sufficient mechanical rigidity. Such rigidity or stiffness aids the use of the energy delivery apparatus as a rail to support and guide other therapeutic devices such as catheters to the desired target location. Accordingly, a relatively stiff material such as stainless steel can also be used as a substantial portion of the conductor.

In some embodiments of the invention, the electrically insulating material is divided into a first electrically insulating material and a second electrically insulating material. A first electrically insulating layer 42 made out of the first electrically insulating material substantially covers a first section of the electrical conductor 16. A second electrically insulating layer 44 made out of the second electrically insulating material substantially covers a second section of the electrical conductor 16. The second section is located distally relatively to the first section. Furthermore, the first and second electrically insulating materials may comprise different materials with differing physical properties. For example, in some embodiments, the second electrically insulating material comprises polyimide, while the first electrically insulating material comprises PTFE. This allows for the second electrically insulating layer 44 to be substantially thinner than the first electrically insulating layer 42, while being sufficiently insulative so as to prevent undesired leakage of current. This substantially increases the flexibility of the energy delivery apparatus 10 substantially adjacent the apparatus distal end 14. In addition, this provides a material that is substantially more lubricious over the wider section of the energy delivery apparatus 10 so as to facilitate movement of the energy delivery apparatus 10 through body vessels and through channels created within the body.

Typically, the first electrically insulating layer 42 substantially covers the conductor wider section 34 and the second electrically insulating layer 44 substantially covers the conductor narrower section 36. However, in alternative embodiments of the invention, the first and second electrically insulating layers 42 and 44 are configured in any other suitable manner. Also, to ensure maximal electrically insulating properties while minimizing stress concentrations that may cause cracks in the electrically insulating layer provided by the first and second electrically insulating layers 42 and 44, in some embodiments of the invention, the first electrically insulating layer 42 substantially overlaps the second electrically insulating layer 44 at their junction. Also, in alternative embodiments of the invention, the electrical conductor 16 is electrically insulated in any other suitable manner.

The capacitance C of a dielectric insulation coating of relative dielectric constant $\in_r$, outer diameter b and inner diameter a is given by $$C=(2\pi\in_0\in_r L)/\ln(b/a)$$

where $\in_0$ is the permittivity of free space and L is the length of the insulation portion. This equation can be used to determine required dielectric coating thicknesses, given desired power delivery levels at the wire tip. A typical length of wire in a patient body is about 1.5 m or less. Then for instance, a coating with thickness 0.0015 inches and dielectric constant 2.5 (an example of such a material is PTFE) over a wire conductor of diameter 0.011 inches and length 1.5 m yields a capacitance value of C=903 pF.

When Radio Frequency (RF) energy is used as the energy source, with frequency possibly in the 0.5 MHz range, this corresponds to a capacitive impedance of about 370 Ω. The impedance due to a lesion at the distal tip electrode of the wire can often be in the range of 3000Ω; the relatively much smaller value of the capacitive impedance means that only about 10% of the input current actually reaches the tip electrode and thence the lesion. For such reasons of potential current leakage due to capacitive coupling, it is important that the wire conductor diameter and the insulation coating thickness as well as the insulation dielectric constant be carefully chosen. The numbers above are given for purposes of non-limiting example only, and a specific embodiment can use values appropriate to a corresponding specific clinical application and/or as dictated by convenience in accordance with the teachings of the present invention.

It is desirable that preferably an insulation coating thickness of at least 0.002 inches, and still more preferably 0.003 inches is used as the insulation coating thickness. It is also preferable that the dielectric coating have a dielectric constant that is smaller than about 3, and more preferably smaller than about 2.5, and still more preferably smaller than about 2. For a 0.014" (outer) diameter guidewire, this means that the conductor wire has a diameter of about 0.010 inches or smaller, and more preferably about 0.008 inches or smaller. As another example, in the case of a 0.018" (outer) diameter guidewire, the conductor wire has a diameter of about 0.014 inches or smaller, and more preferably about 0.012 inches or smaller. In some applications it is desirable to use a wire conductor material that possesses a certain amount of mechanical stiffness. Thus in the case of Nitinol, it is often desirable to use a wire conductor diameter of about 0.012 inches along the major proximal portion of the wire. Equivalently, if stainless steel is used as the wire conductor, it is desirable to use a wire conductor diameter of about 0.008 inches along the major proximal portion of the wire.

The above considerations can also be expressed in terms of ratios. For instance it is preferable that along the major proximal portion of the wire, the ratio of the insulation coating thickness to the wire conductor diameter is greater than about 0.18, and still more preferable that this ratio is greater than about 0.36, in the case of a 0.014" (outer) diameter guidewire. In the case of a 0.018" (outer) diameter guide wire, it is preferable that along the major proximal portion of the wire, the ratio of the insulation coating thickness to the wire conductor diameter is greater than about 0.13, and still more preferable that this ratio is greater than about 0.23.

In some embodiments of the invention, a radiopaque marker is mounted to the electrical conductor 16. In some embodiments of the invention, the radiopaque marker is also the magnetically responsive material present in the guiding elements 26. However, in alternative embodiments of the invention, the radiopaque marker includes a radiopaque material that is distinct from the guiding element 26 and that is secured to conductor 16 or secured or embedded into the electrically insulating layer, among other possibilities. For example, in one embodiment of the invention wherein a radiopaque band is mounted around the electrode at the proximal-most portion of the electrode, and/or a radiopaque band could be mounted under the heat shield. Alternatively, a radiopaque coil could be wrapped around the most distal portion of the energy delivery apparatus.

In some embodiments of the invention, the target location is included in an occlusion, the occlusion at least partially occluding the body vessel. It has been found that many types of body vessels that are typically not accessible using conventional energy delivery apparatuses, such as coronary blood vessels, peripheral blood vessels and cranial blood vessels, among other possibilities, are relatively easily accessible using the energy delivery apparatus. Therefore, the presence of the electrode 22 and of the guiding element 26 in the energy delivery apparatus 10 produce a synergistic effect allowing to perform surgical procedures that were typically not able to be performed using prior art energy delivery apparatuses.

In some embodiments of the invention, the energy delivery apparatus 10 is used such that a channel is created at least partially through the occlusion. This channel may be created by delivering energy through the electrode 22 and advancing the apparatus distal end into the occlusion simultaneously or after delivering energy.

It has been found that the claimed energy delivery apparatus is particularly well suited for creating channels in occlusions that are located at a bifurcation in the body vessel. Indeed, in prior art devices, the presence of the occlusion at the bifurcation typically pushes the apparatus distal end of prior art devices through the non-occluded branch of the body vessel, which therefore makes the creation of channels through the occlusion relatively difficult. By using the magnetic field, the apparatus distal end may be oriented such that the electrode remains substantially adjacent to the occlusion until at least a portion of a channel is created into the occlusion which allows the distal end of the energy delivery apparatus to be received within the occlusion, such that the energy delivery apparatus is guided away from the non-occluded branch.

In specific embodiments of the invention, the electrical conductor 16 is between about 40 centimeters and about 350 centimeters in length. In more specific embodiments of the invention, the electrical conductor 16 is between about 65 centimeters and 265 centimeters in length. The outer diameter of the energy delivery apparatus 10 is typically between about 0.01 inches and about 0.05 inches. In a specific embodiment of the invention, the outer diameter is between about 0.013 inches and about 0.04 inches. In a very specific embodiment of the invention, the electrical conductor 16 has an outer diameter of about 0.0025 inches in the narrower section and 0.012 inches in the wider section. In another very specific embodiment of the invention, the electrical conductor 16 has an outer diameter of about 0.0025 inches in the narrower section and 0.008 inches in the wider section. The electrode is typically less than about 4 millimeters in length.

In some embodiments, the heat shield 28 may be between about 0.05 cm and about 0.20 cm in length, and between 0.025 and about 0.05 cm in thickness. In one particular example, the heat shield material is about 0.1 cm in length, and about 0.035 cm in thickness.

Different methods of affecting the flexibility of the electrical conductor 12 include varying diameter profiles, use of distinct materials in different portions of the conductor, using a material with graded stiffness properties along its length, using dielectric insulation comprising distinct materials along different sections, using dielectric insulation with varying or graded stiffness properties, and the formation of notches in the electrically insulating material, in the electrical conductor 16 or both in the electrical conductor 16 and the electrically insulating material.

In some embodiments of the invention, the magnetically responsive material is welded, soldered, adhered or otherwise attached to the conductor distal end 20.

In some embodiments, an auxiliary device may be advanced to the target location by using the energy delivery apparatus 10 as a guide or a rail. In some such embodiments, the apparatus proximal end may be passed through the auxiliary device, and the auxiliary device may then be advanced together with energy delivery apparatus 10 into the patient's body. In alternate embodiments, the auxiliary device may be inserted over energy delivery apparatus 10 and into the patient's body after energy delivery apparatus 10 has reached the target location. Examples of auxiliary devices include, but are not limited to, catheters, sheaths, dilators, visualization devices, or any other devices having a lumen within which energy delivery apparatus 10 may be disposed.

In some embodiments, the energy delivery apparatus 10 may comprise means for enhancing steerability. Such means may include piezo-actuators or electroactive polymers disposed on the distal region of the energy delivery apparatus 10. For example, a piezo-actuator or electroactive polymer may be disposed on one side of the energy delivery apparatus 10, such that when an electrical field is applied across the piezo-actuator or electroactive polymer, a strain is generated along one side of the energy delivery apparatus 10, causing the energy delivery apparatus 10 to deflect in a desired direction.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present invention has been described hereinabove by way of certain embodiments thereof, it can be modified, without departing from the subject invention as defined in the appended claims.

We claim:

1. An energy delivery apparatus for delivering electrical energy at a target location, said energy delivery apparatus being navigable with an applied magnetic field, the energy delivery apparatus comprising:
an elongate electrical conductor, having a distal section that is narrower than a proximal section;
an electrode for delivering said electrical energy at said target location, the electrode being disposed adjacent the distal end of the distal section of the elongate electrical conductor and being electrically coupled to said electrical conductor;
a first insulating dielectric coating along a substantial portion of the length of the proximal section of the elongate electrical conductor, the insulating dielectric coating having a dielectric constant smaller than about 3;
a second insulating dielectric coating over the distal section of the elongate electrical connector;
at least one guiding element comprising a magnetically responsive material mounted on the distal section of the elongate electrical conductor, over the second insulating dielectric coating, the at least one guiding element being proximal to and spaced from the electrode;
a heat shield on the distal section of the elongate electrical conductor, between the electrode and the least one guiding element; and
a coating over at least a proximal portion of the distal section of the elongate electrical conductor, the coating extending over the at least one guiding element, so that the external diameter of the device adjacent the proximal portion of the distal section of the elongate electrical conductor is substantially the same as the diameter of that device at the proximal section of the elongate electrical conductor.

2. The energy delivery apparatus of claim 1, wherein said first insulating dielectric coating results in a net capacitance value smaller than about 1800 pF across its inner and outer surfaces over a 1.5 meter long section of said energy delivery apparatus.

3. The energy delivery apparatus of claim 1, wherein said first insulating dielectric coating is larger than about 0.002 inches in thickness.

4. The energy delivery apparatus of claim 1, where the ratio of the thickness of the first insulating dielectric coating to the electrical conductor diameter is larger than about 0.36 when the outer diameter of a substantial portion of the energy delivery apparatus is less than 0.0143 inches.

5. The energy delivery apparatus of claim 1, where the ratio of the thickness of the first insulating dielectric coating to the electrical conductor diameter is greater than about 0.23 when the outer diameter of a substantial portion of the energy delivery apparatus is between 0.0143 inches and about 0.0183.

6. The energy delivery apparatus of claim 1, where the first insulating dielectric coating thickness is between about 0.002 inches and about 0.003 inches.

7. The energy delivery apparatus of claim 1, where the first insulating dielectric coating thickness is between about 0.003 inches and about 0.004 inches.

8. The energy delivery apparatus of claim 1, where the first and second insulating dielectric coatings comprise at least two longitudinal sections of distinct dielectric materials.

9. The energy delivery apparatus of claim 1, where the second dielectric coating extends to cover at least a portion of the electrode.

10. The energy delivery apparatus of claim 1, wherein said electrical conductor includes a nickel titanium alloy.

11. The energy delivery apparatus of claim 1, wherein said electrical conductor includes stainless steel.

12. The energy delivery apparatus of claim 1, wherein said electrical conductor includes a proximal portion comprising stainless steel and a distal portion comprising a nickel titanium alloy.

* * * * *